US00PP27677P3

(12) United States Plant Patent
Egger

(10) Patent No.: US PP27,677 P3
(45) Date of Patent: Feb. 14, 2017

(54) ***KNIPHOFIA* PLANT NAMED 'POCO ORANGE'**

(50) Latin Name: ***Kniphofia* spp.**
Varietal Denomination: Poco Orange

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby ( * ) Notice: Subject to any disclaimer, the term of this patent is extended or adjusted under 35 U.S.C. 154(b) by 39 days.

(21) Appl. No.: 14/545,806

(22) Filed: Jun. 22, 2015

(65) Prior Publication Data

US 2016/0374253 P1 Dec. 22, 2016

(51) Int. Cl.
*A01H 5/02* (2006.01)

(52) U.S. Cl.
USPC ..... Plt./443

(58) Field of Classification Search
USPC ..... Plt./443
See application file for complete search history.

*Primary Examiner* — Keith Robinson
(74) *Attorney, Agent, or Firm* — Klarquist Sparkman, LLP; Sheree Lynn Rybak

(57) ABSTRACT

A new and distinct *Kniphofia* plant characterized by its habit of forming multiple crowns fast and each crown produces inflorescences in the first season, large inflorescences of orange flowers with dark tips on short stems, a very long bloom time with repeat blooming from July through October in Canby, Oreg., a short habit, narrow, grassy leaves, and excellent vigor.

1 Drawing Sheet

Botanical denomination: *Kniphofia* spp.
Cultivar designation: 'Poco Orange'.

BACKGROUND OF THE INVENTION

The present invention relates to a new and distinct *Kniphofia*, and given the cultivar name is 'Poco Orange'. *Kniphofia* is in the family Xanthorrhoeaceae. 'Poco Orange' is a hybrid resulting from a planned breeding program to produce short, compact, reblooming *Kniphofia*. The cross was made using the following proprietary, unreleased plants: *Kniphofia* K85-3, as the seed parent and *Kniphofia* K86-1b, as the pollen parent. It was selected for best habit, flower color, reblooming, and crown count from many seedlings of the cross in Canby, Oreg.

Compared to *Kniphofia* K85-3, the seed parent, the new cultivar is more free-flowering and has orange flowers rather than red.

Compared to *Kniphofia* K86-1b, the pollen parent, the new cultivar is more free-flowering.

Compared to *Kniphofia* 'Creamsicle', U.S. Plant Pat. No. 22,489, the new cultivar has larger flowers and inflorescences that are a darker orange color with dark tips rather than creamy red orange.

Compared to *Kniphofia* 'Mango Popsicle', U.S. Plant Pat. No. 22,968, the new cultivar has inflorescences at half the height and orange flowers with dark tips rather than yellow orange flowers.

SUMMARY OF THE INVENTION

The new cultivar is unique and characterized by:

1. its habit of forming multiple crowns fast and each crown produces inflorescences in the first season,
2. large inflorescences of orange flowers with dark tips on short stems, 3. a very long bloom time with repeat blooming from July through October in Canby, Oreg.,
4. a short habit,
5. narrow, grassy leaves, and
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows 6-month-old *Kniphofia* 'Poco Orange' in the ground in the trial field in August in Canby, Oreg.

DETAILED PLANT DESCRIPTION

The following is a detailed description of the new *Kniphofia* cultivar based on observations of 6-month-old specimens growing outside in full sun in Canby, Oreg. These were planted as 4" plants in late May. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* $5^{th}$ edition, 2007.

Plant:

*Type*.—Rhizomatous herbaceous perennial.
*Hardiness*.—USDA Zones 7 to 9.

*Size*.—Grows to 66 cm wide and 40 cm tall from the top of the soil to the top of the foliage.
*Crown #*.—About 30.
*# Leaves/crown*.—About 11.
*# Inflorescences/crown*.—1 to 2.
*Form*.—Clumping.
*Roots*.—Fine to medium in thickness, moderately dense, fibrous; color 158A to 158B.
*Growth rate*.—Vigorous.

Leaf:
*Type*.—Simple, upright aspect.
*Shape*.—Strap-like, keeled.
*Arrangement*.—Basal rosette with about 11 leaves per shoot.
*Blade size*.—22 cm to 47 cm long and 4 mm to 9 mm wide.
*Margins*.—Entire.
*Apex*.—Acuminate.
*Base*.—Clasping.
*Surface texture*.—Glabrous on topside, glaucous on the both sides.
*Venation*.—Parallel.
*Color*.—Top and bottom side Green 137A.

Inflorescence:
*Type*.—Spike-like scapose raceme.
*Number of flowers per raceme*.—About 120.
*Inflorescence*.—11.5 cm long and 5.5 cm wide.
*Peduncle description*.—Strong, grows to 31 cm long and 10 mm wide, glabrous, Yellow Green 146A.
*Pedicle description*.—1.5 mm long and 1 mm wide, glabrous, Yellow Green 146B.
*Bloom time*.—July through October in Canby, Oreg.
*Lastingness*.—An inflorescence lasts for 2 to 4 weeks depending on the temperature.

Flower bud:
*Size*.—29 mm long and 4 mm wide.
*Shape*.—Cylindrical.
*Surface texture*.—Glabrous.
*Color*.—Orange 26C with main veins and tips Orange Red 34A.

Flower:
*Type*.—Actinomorphic.
*Shape*.—Cylindrical and tubular.
*Size*.—Grows to 32 mm deep and 10 mm wide.
*Aspect*.—Side to slightly down facing.
*Texture*.—Waxy.
*Surface texture*.—Glabrous on both sides.
*Corolla description*.—28 mm long and 10 mm wide, 6-lobed fused tepals, tube 26 mm long and 5 mm wide, lobes reflex, each 3 mm wide and 4 mm long, ovate, entire, obtuse to acute, color inside and outside Yellow Orange 22A with main veins Orange Red 34A.
*Pistil description*.—One, 27 mm long and 1.5 mm wide, ovary oblong, 2 mm long 1.5 mm wide, Yellow Green 146C, style 25 mm long, Grayed Yellow 161C, stigma crested, minute, White NN155A.
*Stamen*.—6, 32 mm long, filaments 30.5 mm long and less than 1 mm wide, White 155A, anthers 1.5 mm long and 1 mm wide and Yellow 8A, pollen Yellow 4A, scarce.
*Fragrance*.—None.

Fruit: None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

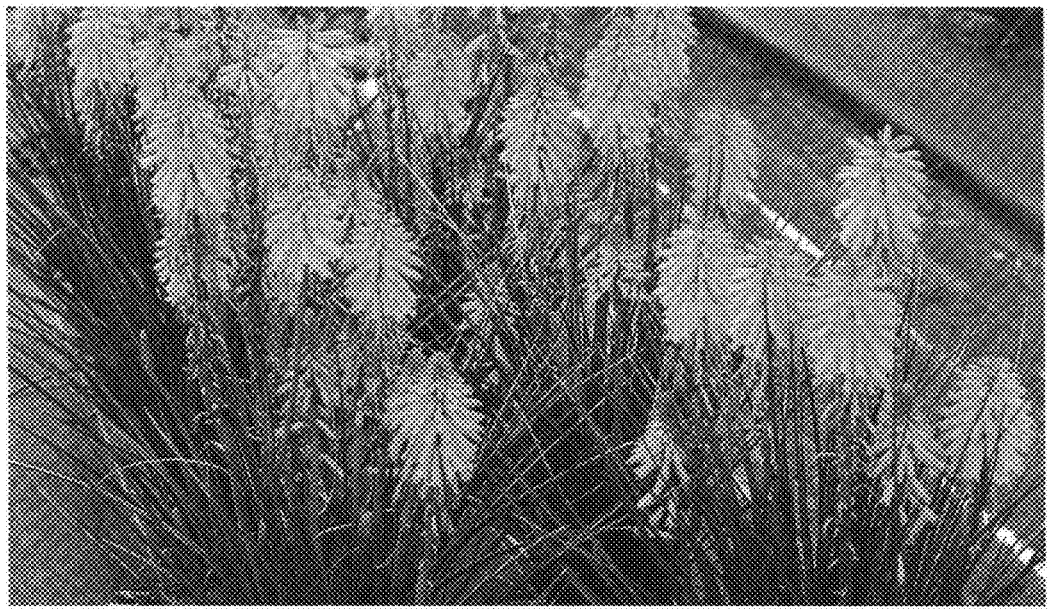

* * * * *